(12) United States Patent
Duncan

(10) Patent No.: US 9,029,543 B2
(45) Date of Patent: May 12, 2015

(54) PROCESS FOR THE SYNTHESIS OF QUATERNARY AMINE COMPOUNDS

(75) Inventor: Scott Duncan, Bedford, MA (US)

(73) Assignee: Alkermes, Inc., Waltham, MA (US)

( * ) Notice: Subject to any disclaimer, the term of this patent is extended or adjusted under 35 U.S.C. 154(b) by 366 days.

(21) Appl. No.: 13/440,584

(22) Filed: Apr. 5, 2012

(65) Prior Publication Data

US 2012/0258981 A1 Oct. 11, 2012

Related U.S. Application Data

(60) Provisional application No. 61/472,016, filed on Apr. 5, 2011.

(51) Int. Cl.
C07D 221/28 (2006.01)
C07D 489/08 (2006.01)

(52) U.S. Cl.
CPC ..................... C07D 489/08 (2013.01)

(58) Field of Classification Search
USPC .......................................................... 546/74
See application file for complete search history.

(56) References Cited

U.S. PATENT DOCUMENTS

| | | | |
|---|---|---|---|
| 3,856,795 | A | 12/1974 | Yardley |
| 3,957,793 | A | 5/1976 | Wentland et al. |
| 4,032,529 | A | 6/1977 | Wentland et al. |
| RE29,943 | E | 3/1979 | Wentland et al. |
| 4,176,186 | A | 11/1979 | Goldberg et al. |
| 4,205,171 | A | 5/1980 | Albertson |
| 4,464,378 | A | 8/1984 | Hussain |
| 4,649,200 | A | 3/1987 | Portoghese et al. |
| 5,258,386 | A | 11/1993 | Newman et al. |
| 5,607,941 | A | 3/1997 | Merz et al. |
| 6,166,232 | A | 12/2000 | Bergfeld et al. |
| 6,365,594 | B1 | 4/2002 | Dondio et al. |
| 6,451,806 | B2 | 9/2002 | Farrar |
| 6,784,187 | B2 | 8/2004 | Wentland |
| 6,812,236 | B2 | 11/2004 | Gibson et al. |
| 6,887,998 | B2 | 5/2005 | Wentland |
| 7,057,035 | B2 | 6/2006 | Wentland et al. |
| 7,244,866 | B2 | 7/2007 | Carson et al. |
| 7,262,298 | B2 | 8/2007 | Wentland |
| 7,265,226 | B2 | 9/2007 | Wentland |
| 7,645,880 | B2 | 1/2010 | Dlubala |
| 8,101,756 | B2 * | 1/2012 | Eipert et al. ............... 546/45 |
| 8,263,807 | B2 * | 9/2012 | Wentland ................. 564/163 |
| 2002/0099216 | A1 | 7/2002 | Gibson et al. |
| 2007/0021457 | A1 | 1/2007 | Wentland |
| 2010/0035910 | A1 | 2/2010 | Wang et al. |

FOREIGN PATENT DOCUMENTS

| | | | |
|---|---|---|---|
| EP | 0632041 | A1 | 1/1995 |
| EP | 0254120 | A2 | 1/1998 |
| GB | 1340720 | | 12/1973 |
| WO | 93/11761 | A1 | 6/1993 |
| WO | 97/25331 | A1 | 7/1997 |
| WO | 98/52929 | A1 | 11/1998 |
| WO | 02/36573 | A2 | 5/2002 |
| WO | 03/101963 | A1 | 12/2003 |
| WO | 2009023567 | A1 | 2/2009 |
| WO | 2010141666 | A2 | 12/2010 |

OTHER PUBLICATIONS

Wentland et. al., 3-Carboxamido analogues of morphine and naltrexone. synthesis and opioid receptor binding properties, Bioorg Med Chem Lett. Jul. 9, 2001;11(13):1717-21.
Wentland et. al., 8-Carboxamidocyclazocine analogues: redefining the structure-activity relationships of 2,6-methano-3-benzazocines, Bioorg Med Chem Lett. Mar. 12, 2001;11(5):623-6.
Bidlack et. al., 8-Carboxamidocyclazocine: a long-acting, novel benzomorphan, J Pharmacol Exp Ther. Jul. 2002;302 (1):374-80.
Wentland et. al., 8-Aminocyclazocine analogues: synthesis and structure-activity relationships, Bioorg Med Chem Lett. Jan. 17, 2000;10(2):183-7.
Wentland et. al., Redefining the structure-activity relationships of 2,6-methano-3-benzazocines. Part 2: 8-formamidocyclazocine analogues, Bioorg Med Chem Lett. Jun. 2, 2003;13(11):1911-4.
Wentland et. al., Synthesis and opioid receptor binding properties of a highly potent 4-hydroxy analogue of naltrexone, Bioorg Med Chem Lett. Apr. 15, 2005;15(8):2107-10.
Wentland et. al., Redefining the structure-activity relationships of 2,6-methano-3-benzazocines. 4. Opioid receptor binding properties of 8-[N-(4'-phenyl)-phenethyl)carboxamido] analogues of cyclazocine and ethylketocyclazocine, J Med Chem. Sep. 7, 2006;49(18):5635-9.
Vanalstine et. al., Redefining the structure-activity relationships of 2,6-methano-3-benzazocines. 5. Opioid receptor binding properties of N-((4'-phenyl)-phenethyl) analogues of 8-CAC, Bioorg Med Chem Lett. Dec. 1, 2007;17 (23):6516-20.
Wentland et. al., Redefining the structure-activity relationships of 2,6-methano-3-benzazocines. 6: Opioid receptor binding properties of cyclic variants of 8-carboxamidocyclazocine, Bioorg Med Chem. May 15, 2008;16(10):5653-64.
Wentland et. al., Syntheses and opioid receptor binding properties of carboxamido-substituted opioids, Bioorg Med Chem Lett. Jan. 1, 2009;19(1):203-8.
Wentland et. al., Redefining the structure-activity relationships of 2,6-methano-3-benzazocines. Part 7: syntheses and opioid receptor properties of cyclic variants of cyclazocine. Bioorg Med Chem Lett. Jan. 15, 2009;19(2):365-8.
Wentland et. al., Syntheses of novel high affinity ligands for opioid receptors, Bioorg Med Chem Lett. Apr. 15, 2009;19(8):2289-94.

(Continued)

*Primary Examiner* — Charanjit Aulakh
(74) *Attorney, Agent, or Firm* — Elmore Patent Law Group, P.C.; Roy P. Issac; Carolyn S. Elmore

(57) ABSTRACT

The invention relates to a process for the synthesis of quaternized compounds of formula:

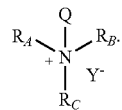

13 Claims, No Drawings

(56) References Cited

OTHER PUBLICATIONS

McCurdy et. al., Investigation of phenolic bioisosterism in opiates: 3-sulfoxamido analogues of naltrexone and oxymorphone, Organic Letters, 2(6)819-821, 2000.

Danso-Danquah, R, Synthesis and sigma binding properties of 1'- and 3'-halo- and 1',3'-dihalo-N-normetazocine analogues, J Med Chem. Jul. 21, 1995;38(15):2986-9.

Diaz et. al., SAR and biological evaluation of novel trans-3,4-dimethyl-4-arylpiperidine derivatives as opioid antagonists., Bioorg Med Chem Lett. Sep. 1, 2005;15(17):3844-8.

Ida et. al., The Nonnarcotic Antitussive Drug Dimemorfan: A Review, Clin Ther. Mar.-Apr. 1997;19(2):215-31.

Mohaschi et. al., Acylmorphinans. A Novel Class of Potent Analgesic Agents, Journal of Medicinal Chemistry, 1985, 28(9) 1177-80.

Wentland et. al., Selective Protection and Functionalization of Morphine: Syntheses and Opioid Receptor Binding Properties of 3-Amino3-desoxymorphine Derivatives, Journal of Medicinal Chemistry, 43, (2000), 3558-3565.

Zaveri N. et. al., Small-Molecule Agonists and Antagonists of the Opioid Receptor-Like Receptor (ORL1, NOP): Ligand-Based Analysis of Structural Factors Influencing Instrinsic Activity at NOP, The AAPS Journal, 7(2): 2005, E345-E352.

Sayre et. al., Design and Synthesis of Naltrexone-Derived Affinity Labels with Nonequilibrium Opioid Agonist and Antagonist Activities. Evidence for the Existence of Different $\mu$ Receptor Subtypes in Different Tissues, Journal of Medicinal Chemistry, 27 (1984), 1325-1335.

Zhang et. al., 10-Ketomorphinan and 3-Substituted-3-desoxymorphinan Analogues as Mixed $\kappa$ and $\mu$ Opioid Ligands: Synthesis and Biological Evaluation of Their Binding Affinity at Opioid Receptors, Journal of Medicinal Chemistry, 47 (2004), 165-174.

Vanalstine, M. Thesis, Design, Synthesis and evaluation of novel N-substituted derivatives of 8-carboxamidocyclazocine, Apr. 2007.

Arrington, et al., Bioorganic and Medicinal Chemistry Letters 14, pp. 1807-1809 (2004).

\* cited by examiner

PROCESS FOR THE SYNTHESIS OF QUATERNARY AMINE COMPOUNDS

RELATED APPLICATION(S)

This application claims the benefit of U.S. Provisional Application No. 61/472,016, filed on Apr. 5, 2011. The entire teachings of the above application is incorporated herein by reference.

BACKGROUND OF THE INVENTION

Quaternary ammonium compounds can be synthesized from their perspective tertiary amines by alkylation. However, the synthesis of quaternary ammonium compounds often results in low yield due to incomplete reactions and unwanted side reactions. The presence of unreacted tertiary amines or side products can make purification difficult. Side reactions include Hofmann elimination and rearrangement reactions. Quaternary ammonium salts react readily under transfer of alkyl groups or under Hofmann elimination under basic conditions. Frequently, both reactions are observed in parallel. (U.S. Pat. No. 6,166,232).

Opiates are a class of compounds in which many of the compounds contain a tertiary nitrogen that can be quaternized to modulate their mode of action. Opiates have been the subject of intense research since the isolation of morphine in 1805, and thousands of compounds having opiate or opiate-like activity have been identified. Among the well known quaternized morphinan compounds is methyl naltrexone (RELISTOR®) used for reducing some of the side effects of opiate drugs. (Goldberg et al., U.S. Pat. No. 4,176,186; Dlubala A, U.S. Pat. No. 7,645,880).

Morphinans are known to undergo ring Hofmann elimination and ring opening to result in tricyclic compounds under base catalyzed quaternization process. (Arrington et al., *Bioorganic & Medicinal Chemistry Letters* 14 (2004) 1807-1809). Anastasia et al., reports ring opening.

SUMMARY OF THE INVENTION

The invention relates to a method for preparing quaternary ammonium compound from their perspective tertiary amines. The invention further relates to quaternization of tertiary amines using alkylating agents including alkyl halides. In some embodiments, the invention relates to the synthesis of a compound of Formula IA by quaternization of a compound of Formula I:

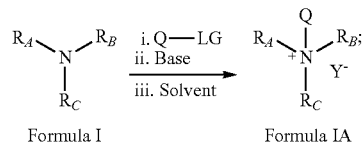

Formula I        Formula IA wherein, Each $R_A$, $R_B$ and $R_C$ is independently is selected from aliphatic, substituted aliphatic, aryl, substituted aryl, heterocyclyl, substituted heterocyclyl, —C(O)$R_{20}$, —C(O)OR$_{20}$, —C(O)NR$_{20}$R$_{21}$, or —N(R$_{20}$)C(O)R$_{21}$; or alternatively $R_A$, $R_B$, and/or $R_C$ together with the nitrogen they are attached to form one, two or three optionally substituted ring(s);

wherein each $R_{20}$ and $R_{21}$ is independently selected from absent, hydrogen, halogen, —OH, —SH, —NH$_2$, —CF$_3$, —CN, —NO$_2$, —N$_3$, —C(O)OH, —C(O)NH$_2$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl;

Q is aliphatic, substituted aliphatic, aryl, substituted aryl, heterocyclyl or substituted heterocyclyl; and, Y— is a counterion;

wherein the quaternization process comprises the step of reacting a compound of Formula I with Q-LG in the presence of a base and a solvent, wherein LG is a leaving group; wherein said solvent is a biphasic solvent, or at least said compound of Formula IA is insoluble in said solvent.

In another embodiment, the present invention is relates to a method of treating opioid induced constipation in a patient comprising the step of administering a composition comprising a quaternized compound (Formula IIA) that is essentially free of the corresponding non-quaternized compound (Formula II). In one embodiment, the weight ratio of Formula IIA to Formula II is more than about 100:1 preferably more than about 150:1, more preferably more than about 200:1, more preferably more than about 250:1, more preferably more than about 400:1. In one embodiment, the weight ratio between Formula IIA and Formula II (Formula IIA/Formula II) is between about 100:1 to about 10,000:1. Preferably, weight the ratio between Formula IIA and Formula II is between about 150:1 to about 10,000:1, preferably between about 200:1 to about 10,000:1, preferably between about 250:1 to about 10,000:1. In a further embodiment, the present invention relates to a unit dose form comprising about 10 to about 100 mg of a compound of quaternized compound (Formula IIA) and about 0 to about 0.25 mg of a compound of non-quaternized compound Formula II.

DETAILED DESCRIPTION OF THE INVENTION

The invention relates to a method for preparing quaternary ammonium compound from their perspective tertiary amines. The invention further relates to quaternization of tertiary amines using alkylating agents including alkyl halides. In some embodiments, the invention relates to the synthesis of a compound of Formula IA by quaternization of a compound of Formula I:

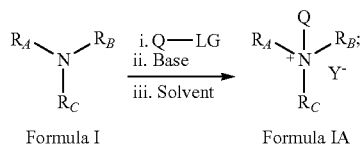

Formula I        Formula IA wherein, Each $R_A$, $R_B$ and $R_C$ is independently is selected from aliphatic, substituted aliphatic, aryl, substituted aryl, heterocyclyl, substituted heterocyclyl, —C(O)$R_{20}$, —C(O)OR$_{20}$, —C(O)NR$_{20}$R$_{21}$, or —N(R$_{20}$)C(O)R$_{21}$; or alternatively $R_A$, $R_B$, and/or $R_C$ together with the nitrogen they are attached to form one, two or three optionally substituted ring(s);

wherein each $R_{20}$ and $R_{21}$ is independently selected from absent, hydrogen, halogen, —OH, —SH, —NH$_2$, —CF$_3$, —CN, —NO$_2$, —N$_3$, —C(O)OH, —C(O)NH$_2$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl;

Q is aliphatic, substituted aliphatic, aryl, substituted aryl, heterocyclyl or substituted heterocyclyl; and, Y— is a counterion, preferably a halogen, substituted or unsubstituted alkylsulfonyl, substituted or unsubstituted arylsulfonyl, aliphatic, substituted aliphatic, aryl, substituted aryl, heterocyclyl or substituted heterocyclyl;

wherein the quaternization process comprises the step of reacting a compound of Formula I with Q-LG in the presence of a base and a solvent, wherein LG is a leaving group; wherein said solvent is a biphasic solvent, or at least said compound of Formula IA is insoluble in said solvent.

In one embodiment, the solubility of a compound of Formula IA in reaction solvent is less than 100 g/L of solvent, preferably less than 50 g/L of solvent, preferably 25 g/L of solvent, preferably 10 g/L of solvent, preferably 5 g/L of solvent, preferably 3 g/L of solvent, preferably 2 g/L of solvent, or preferably 1 g/L of solvent. In one embodiment, at least about 50-100% of the quaternized reaction product precipitates out of the reaction solvent, preferably about 80-100%. In one embodiment the solubility of the compound of Formula IA or IIA is between 100 g/L of solvent to 0 g/L of solvent, preferably between 10 g/L of solvent to 0 g/L of solvent, preferably between 5 g/L of solvent to 0 g/L of solvent.

In one embodiment, the reaction solvent is a polar aprotic solvent or a non-polar solvent. In one embodiment the polar aprotic solvent is selected from dichloromethane, tetrahydrofuran, ethyl acetate, acetone, N,N-dimethylformamide, acetonitrile, sulfolane, dimethylacetamide, N-methylpyrrolidine-2-one, isopropyl acetate, dimethylsulfoxide and mixtures thereof.

In one embodiment, a compound of Formula II is reacted with an alkylating agent, Q-LG, in the presence of an aqueous base:

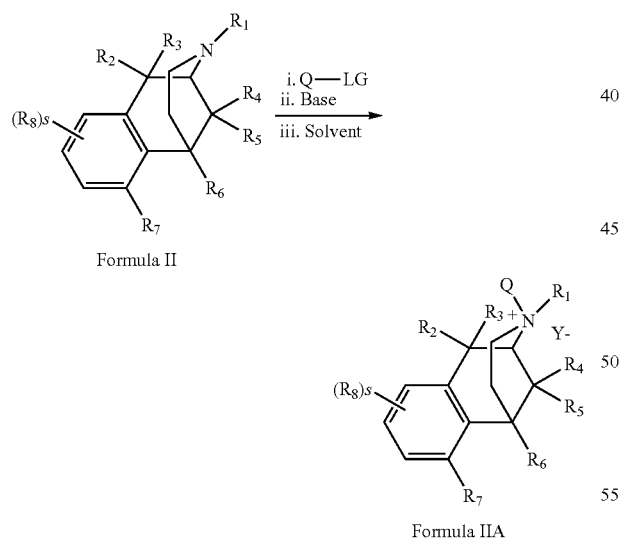

Formula II

Formula IIA wherein, s is 0, 1, 2 or 3;

Y— is a pharmaceutically acceptable counterion, preferably a halogen, substituted or unsubstituted alkylsulfonyl, substituted or unsubstituted arylsulfonyl, aliphatic, substituted aliphatic, aryl, substituted aryl, heterocyclyl or substituted heterocyclyl;

each $R_1$, $R_2$, $R_3$, $R_4$, $R_5$, $R_6$, $R_7$ and $R_8$ is independently selected from absent, hydrogen, halogen, —$OR_{20}$, —$SR_{20}$, —$NR_{20}R_{21}$, —$C(O)R_{20}$, —$C(O)OR_{20}$, —$C(O)NR_{20}R_{21}$, —$N(R_{20})C(O)R_{21}$, —$CF_3$, —CN, —$NO_2$, —$N_3$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl, substituted aryl, heterocyclyl or substituted heterocyclyl; Alternatively, two or more of $R_2$, $R_3$, $R_4$, $R_5$, $R_6$, $R_7$ and $R_8$ together with the atoms they are attached to form one, two, three or four additional optionally substituted ring(s);

alternatively $R_2$ and $R_3$ together with the carbon they are attached to form a C=X group;

wherein each $R_{20}$ and $R_{21}$ is independently selected from absent, hydrogen, halogen, —OH, —SH, —$NH_2$, —$CF_3$, —CN, —$NO_2$, —$N_3$, —C(O)OH, —$C(O)NH_2$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl;

X is S, O or $C(R_{20})(R_{21})$; and,

Q is aliphatic, substituted aliphatic, aryl, substituted aryl, heterocyclyl or substituted heterocyclyl.

In one embodiment, a compound of Formula III is reacted with an alkylating agent, Q-LG, in the presence of an aqueous base to give a compound of Formula IIIA:

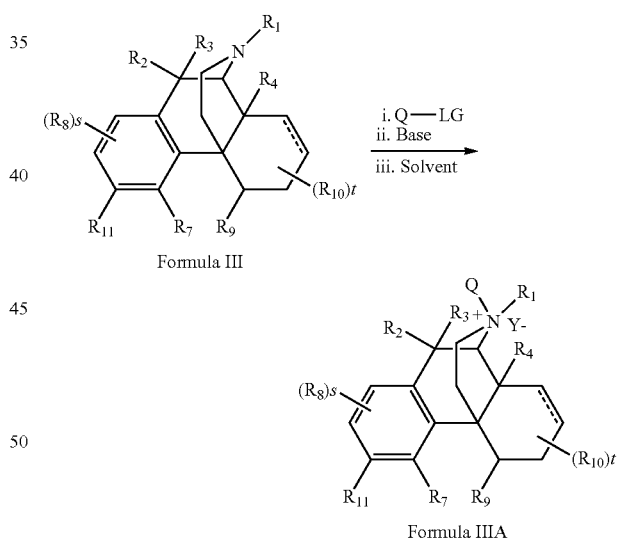

Formula III

Formula IIIA wherein, s, Y—, $R_1$, $R_2$, $R_3$, $R_4$, $R_7$, $R_8$, $R_{20}$, and $R_{21}$ are as defined above;

t is 0, 1, 2, 3, 4, 5, 6, or 7;

each $R_9$, $R_{10}$ and $R_{11}$ is independently selected from absent, hydrogen, halogen, —$OR_{20}$, —$SR_{20}$, —$NR_{20}R_{21}$, —$C(O)R_{20}$, —$C(O)OR_{20}$, —$C(O)NR_{20}R_{21}$, —$N(R_{20})C(O)R_{21}$, —$CF_3$, —CN, —$NO_2$, —$N_3$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl, substituted aryl, heterocyclyl or substituted heterocyclyl;

alternatively two $R_{10}$ groups together with the carbon they are attached to form a C=X group alternatively two $R_{10}$ groups together with the atoms they are attached to, form an additional ring with optional substitution;

alternatively $R_7$ and $R_9$ together with the atoms they are attached to, form an additional ring.

alternatively $R_8$ and $R_{11}$ together with the atoms they are attached to, form an additional ring with optional substitution.

In a preferred embodiment, $R_{11}$ is selected from —$OR_{20}$, $SR_{20}$, —$CON(R_{20})(R_{21})$ and —$CSN(R_{20})(R_{21})$; more preferably, —$CONH_2$, —$OCH_3$ or —OH.

In a preferred embodiment, $R_7$ is —$OR_{20}$; more preferably, —OH.

In one embodiment, a compound of Formula IV is reacted with an alkylating agent, Q-LG, in the presence of an aqueous base to give a compound of Formula IVA:

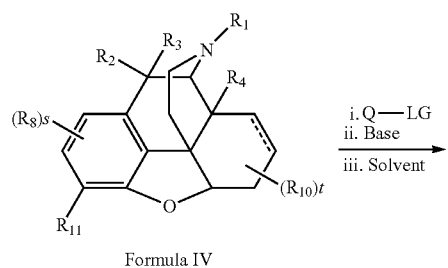

Formula IV

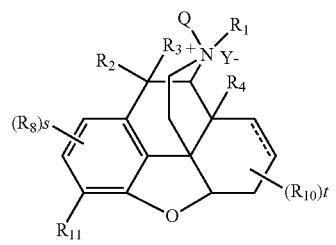

Formula IVA wherein, s, t, Y—, $R_1$, $R_2$, $R_3$, $R_4$, $R_8$, $R_{10}$, $R_{11}$, $R_{20}$, and $R_{21}$ are as defined above.

In one embodiment, a compound of Formula V is reacted with an alkylating agent, Q-LG, in the presence of an aqueous base to give a compound of Formula VA:

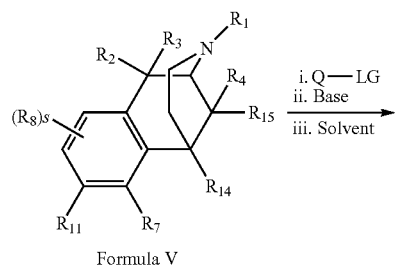

Formula V

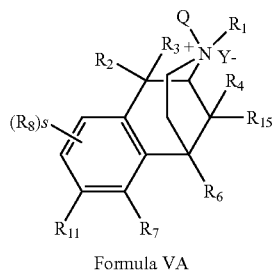

Formula VA wherein, s, t, Y—, $R_1$, $R_2$, $R_3$, $R_4$, $R_8$, $R_{10}$, $R_{11}$, $R_{20}$, and $R_{21}$ are as defined above;

$R_{14}$ and $R_{15}$ are independently selected from alkyl, substituted alkyl, aryl and substituted aryl.

In some embodiments the invention relates to methylation of morphinan and benzomorphan compounds as shown in Processes 1-23 below:

Process 1:

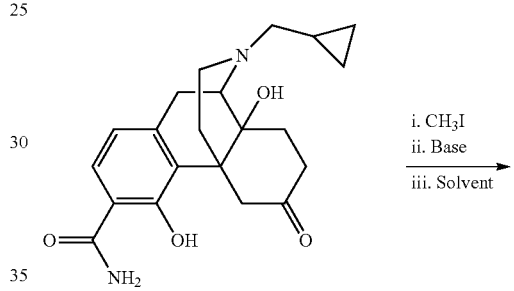

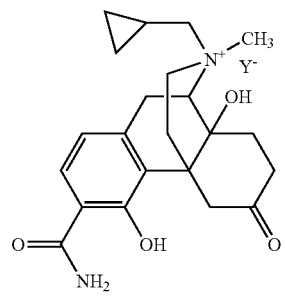

Process 2:

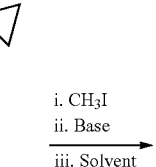

7
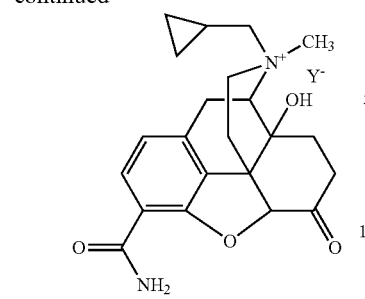
Process 3:
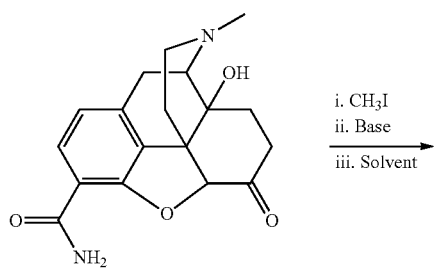 i. CH₃I
ii. Base
iii. Solvent →
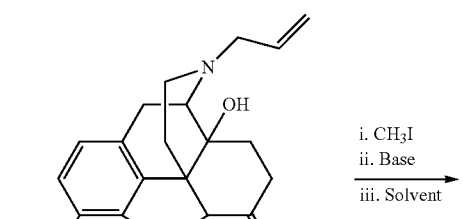
Process 4:
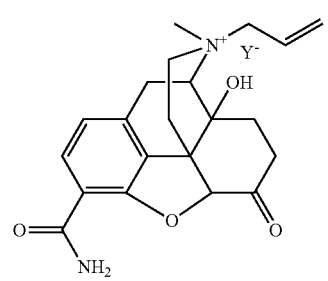 i. CH₃I
ii. Base
iii. Solvent →
8
Process 5:
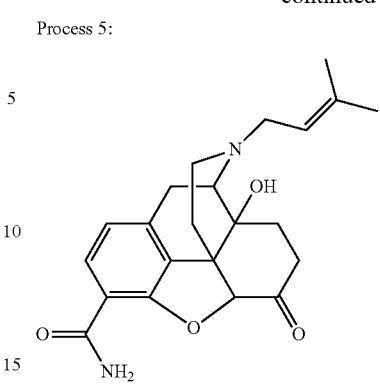 i. CH₃I
ii. Base
iii. Solvent →
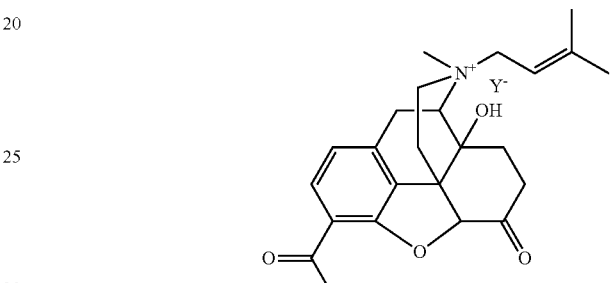
Process 6:
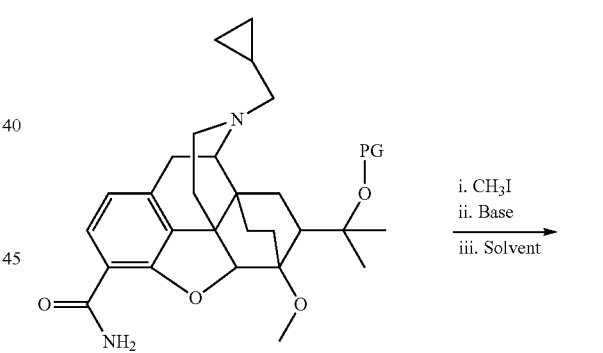 i. CH₃I
ii. Base
iii. Solvent →
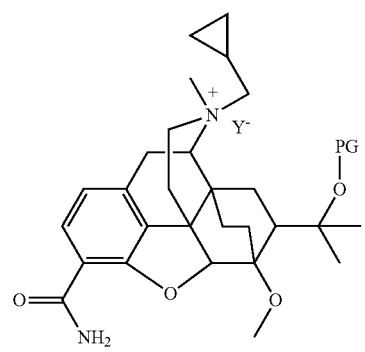

Process 7:
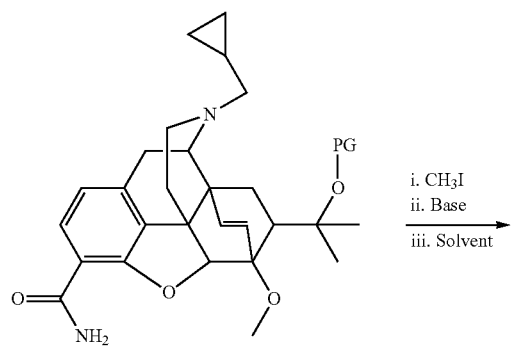
i. CH₃I
ii. Base
iii. Solvent
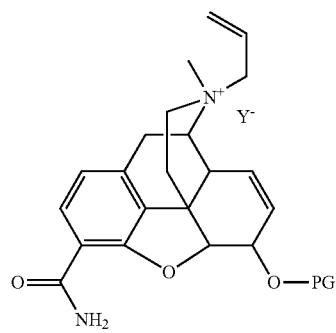
Process 10:
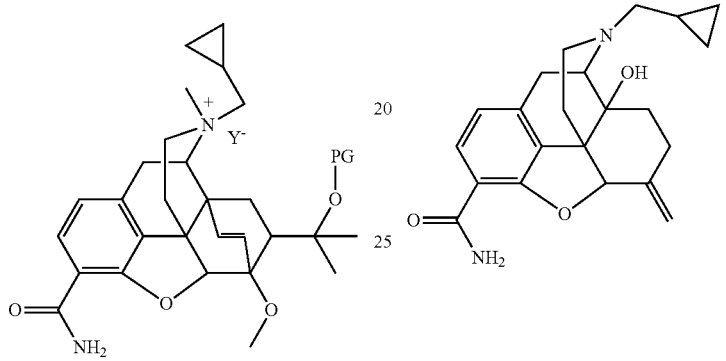
Process 8:
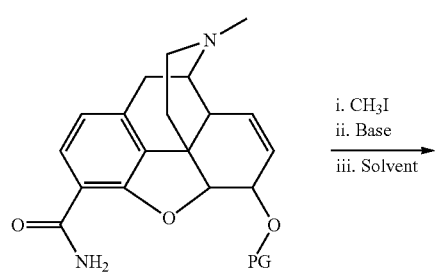
i. CH₃I
ii. Base
iii. Solvent
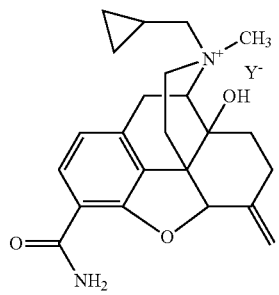
Process 11:
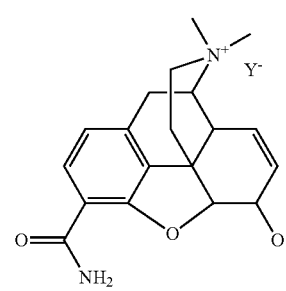
i. CH₃I
ii. Base
iii. Solvent
Process 9:
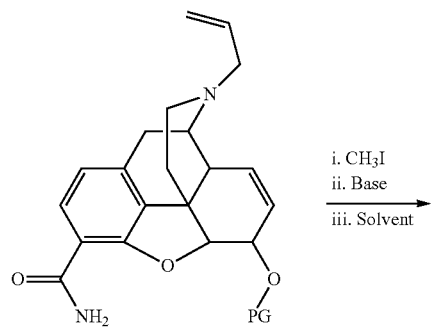
i. CH₃I
ii. Base
iii. Solvent
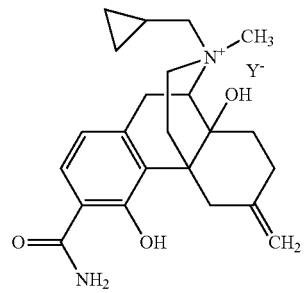

-continued
Process 12:
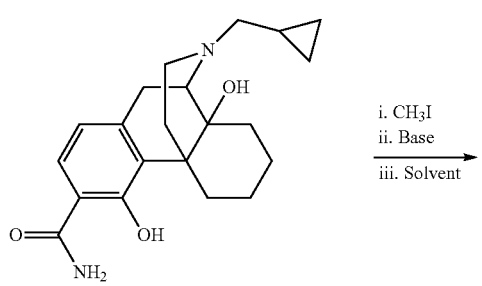
i. CH₃I
ii. Base
iii. Solvent
→
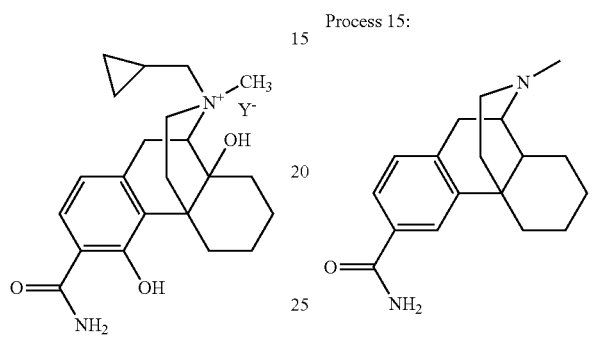
Process 13:
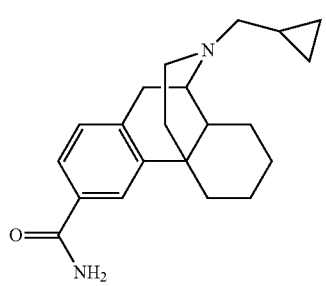
i. CH₃I
ii. Base
iii. Solvent
→
Process 14:
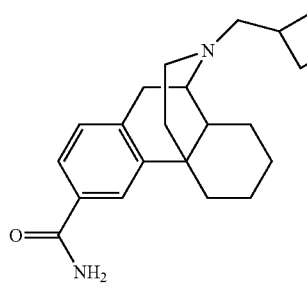
i. CH₃I
ii. Base
iii. Solvent
→
-continued
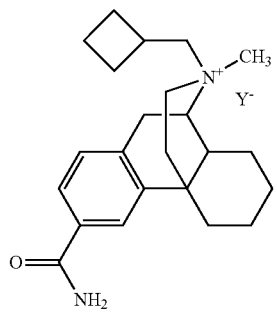
Process 15:
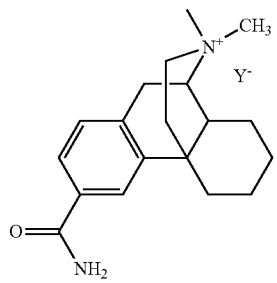
i. CH₃I
ii. Base
iii. Solvent
→
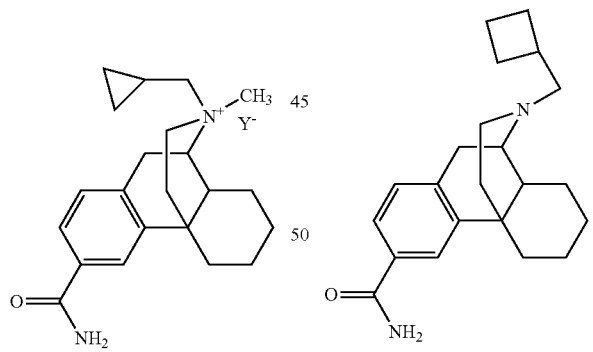
Process 16:
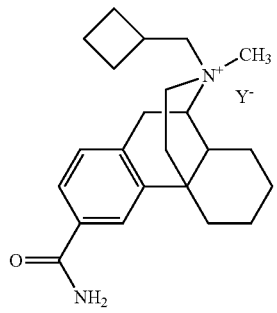

-continued
Process 17:
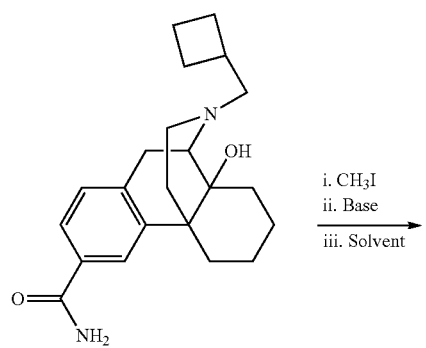 i. CH₃I
ii. Base
iii. Solvent
→
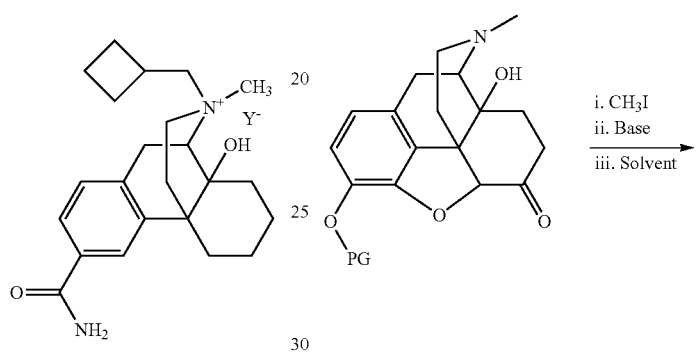
Process 18:
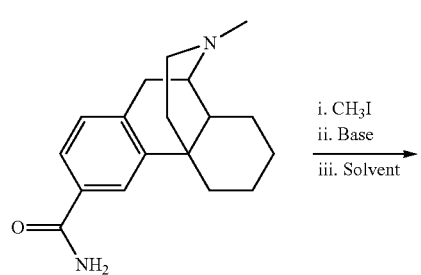 i. CH₃I
ii. Base
iii. Solvent
→
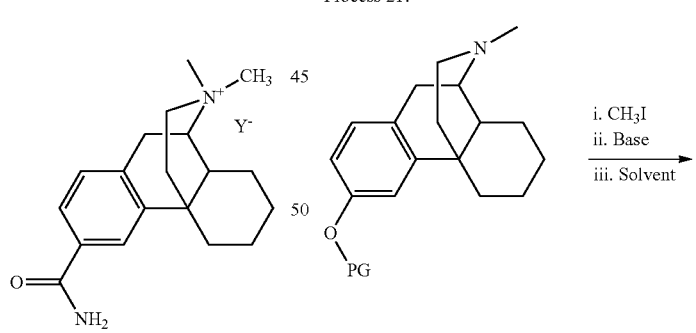
Process 19:
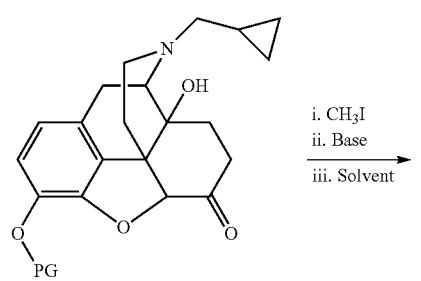 i. CH₃I
ii. Base
iii. Solvent
→
-continued
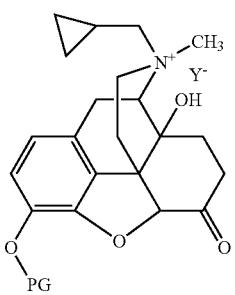
Process 20:
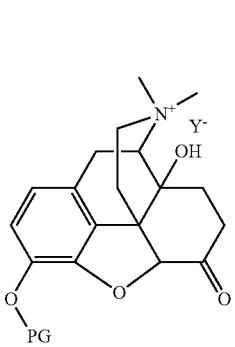 i. CH₃I
ii. Base
iii. Solvent
→
Process 21:
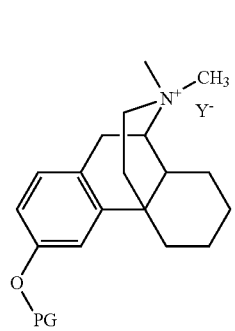 i. CH₃I
ii. Base
iii. Solvent
→

Process 22:

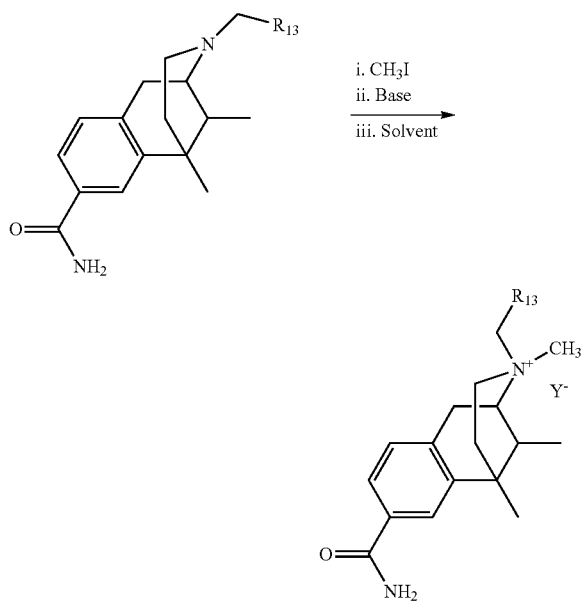

Process 23:

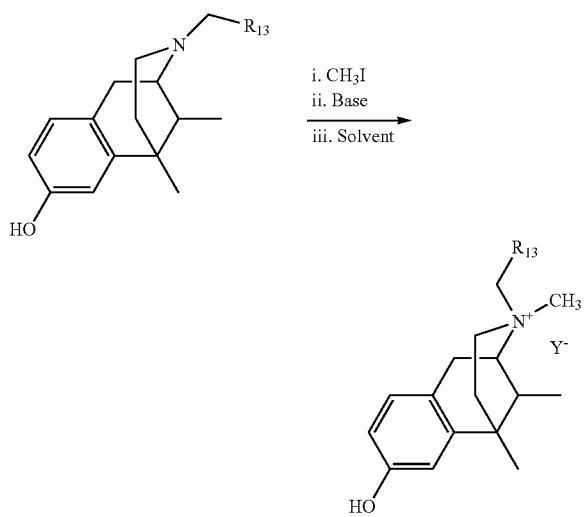

wherein R$_{13}$ is selected from H, cyclopropyl, cyclobutyl, phenyl, —CH═CH$_2$, —CH═C(CH$_3$)$_2$.

wherein PG is a protecting group; and Y— is a counterion, preferably a halogen, substituted or unsubstituted alkylsulfonyl, substituted or unsubstituted arylsulfonyl, aliphatic, substituted aliphatic, aryl, substituted aryl, heterocyclyl or substituted heterocyclyl.

In one embodiment the leaving group and the counterion are the same.

In one embodiment, Q-LG is insoluble in the reaction solvent. In one embodiment, the compound of Formula I-V is insoluble in the reaction solvent. In one embodiment, both Q-LG and the compound of Formula I-V are insoluble in the reaction solvent.

In one embodiment, the base is selected from triethyl amine, dimethyl amine, tert-butyl amine, aqueous ammonia, sodium hydroxide, calcium hydroxide, magnesium hydroxide, potassium hydroxide, lithium hydroxide, sodium carbonate, potassium carbonate, lithium carbonate, sodium bicarbonate, potassium bicarbonate, sodium tert-butoxide, sodium isopropoxide and potassium tert-butoxide.

In one embodiment, Q-LG is an alkyl halide. In one embodiment, a compound of Formula I-V is reacted with Q-LG, where Q-LG is CH$_3$-LG, and LG is selected from bromide, chloride, iodide or —CH$_3$OSO$_3$. In one embodiment, a compound of Formula I-V is reacted with Q-LG, where Q-LG is CH$_3$CH$_2$-LG, and LG is selected from bromide, chloride, iodide, aryl sulfonate or alkyl sulfonate, preferably, mesylate and tosylate.

In another embodiment, the present invention is relates to a method of treating opioid induced constipation in a patient comprising the step of administering a composition comprising a quaternized compound (Formula IIA) that is essentially free of the corresponding non-quaternized compound (Formula II). In one embodiment, the weight ratio of Formula IIA to Formula II is less than about 100:1 preferably more than about 150:1, more preferably more than about 200:1, more preferably more than about 250:1, more preferably more than about 400:1. (For example, a ratio of 100:1 as described herein represents a composition containing 100 g of a compound of Formula IIA and 1 g of a compound of Formula II). In one embodiment, the weight ratio between Formula IIA and Formula II (Formula IIA/Formula II) is between about 100:1 to about 10,000:1. Preferably the weight ratio between Formula IIA and Formula II is between about 150:1 to about 10,000:1, preferably between about 200:1 to about 10,000:1, preferably between about 250:1 to about 10,000:1. In a further embodiment, the present invention relates to a unit dose form comprising about 10 to about 100 mg of a compound of quaternized compound (Formula IIA) and about 0 to about 0.25 mg of a compound of non-quaternized compound Formula II.

In one embodiment, the invention relates to a method of treating or preventing opioid induced constipation in a patient comprising the step of administering a composition comprising a compound of Formula IIA wherein said compound of Formula IIA is synthesized by the process described herein. Without being bound to any particular theory, Formula IIA has an impurity of Formula II, roughly equivalent to 0.2 mgs in the 100 mg dose. The compound of Formula II is a novel opioid receptor µ antagonist and a partial agonist/antagonist at both δ and κ receptors and has a central nervous system (CNS) mechanism of action.

In one embodiment, the invention relates to a method for treating or preventing opioid-induced side effects comprising administering to a patient a compound of Formula IIA, wherein said compound is prepared by a method described herein, in an amount effective to treat the opioid-induced side effect. In one embodiment of the invention the compound is administered to a patient that is chronically administered opioids. In another embodiment the patient is acutely administered opioids. The opioid-induced side effect is preferably selected from a group consisting of constipation, post-operative ileus, immune suppression, inhibition of gastrointestinal motility, inhibition of gastric emptying, nausea, emesis, incomplete evacuation, bloating, abdominal distension, increased gastroesophageal reflux, hypotension, bradycardia, gastrointestinal dysfunction, pruritus, dysphoria, and urinary retention. In one preferred embodiment the opioid-induced side effect is constipation. In another preferred embodiment the opioid-induced side effect is inhibition of gastrointestinal motility or inhibition of gastric emptying. In yet another preferred embodiment the opioid-induced side effect is nausea or emesis. In yet another preferred embodiment the opioid-induced side effect is pruritus. In yet another preferred embodiment the opioid-induced side effect is dysphoria. In yet another preferred embodiment the opioid-induced side effect is urinary retention.

In one embodiment, the invention is directed to methods for preventing and treating the inhibition of gastrointestinal motility, particularly constipation that arises in the group of patients taking chronic or maintenance doses of opioids by administering a composition comprising a compound of Formula IIA wherein said compound of Formula IIA is synthesized by a process described herein. These patients include late stage cancer patients, elderly patients with osteoarthritic changes, methadone maintenance patients, neuropathic pain and chronic back pain patients. Treatment of these patients can reduce complications arising from chronic constipation, such as hemorrhoids, appetite suppression, mucosal breakdown, sepsis, colon cancer risk, and myocardial infarction. Preferred side effects to be treated include constipation and gastrointestinal motility inhibition, dysphoria, pruritus, and urinary retention.

In one embodiment, the invention relates to a method of treating or preventing opioid-induced dysphoria, opioid-induced pruritus, opioid-induced urinary retention, opioid- or nonopioid-induced inhibition of gastric emptying by enteric feeding, and opioid- or nonopioid-induced constipation by administering a composition comprising a compound of Formula IIA wherein said compound of Formula IIA is synthesized by a process described herein.

In one embodiment, the invention relates to the use of a compound of Formula IIA prepared according to a method of processes 1-22 in the preparation of a pharmaceutically administrable medicament for the treatment of post-operative ileus or for the treatment of opioid-induced constipation. In one embodiment, the invention relates to a method of treating opioid induced constipation in a patient comprising the step of administering a composition comprising a compound of Formula IIA and a compound of Formula II wherein the molar ratio of Formula IIA to Formula II is more than 100:1. In one embodiment, the molar ratio of Formula IIA to Formula II is more than 250:1. In one embodiment, the molar ratio of Formula IIA to Formula II is more than 300:1 In one embodiment, the molar ratio of Formula IIA to Formula II is more than 500:1.

In one embodiment, the invention relates a composition comprising a compound of formula:

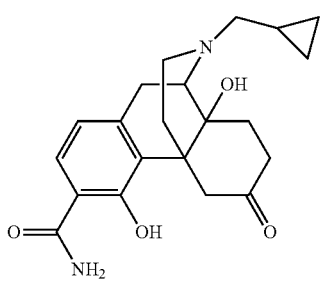 [SMILES: NC(=O)c1ccc2c(c1O)C13CCN(CC4CC4)C(C2)C1(O)CCC(=O)C3]

and, a quaternized compound of formula:

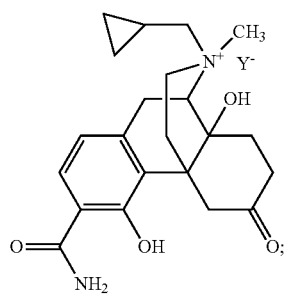

wherein the molar ratio of quaternized compound to the corresponding non-quaternized compound is about 100:1 to about 10,000:1; preferably between about 150:1 to about 10,000:1; preferably between about 200:1 to about 10,000:1.

In one embodiment, the invention relates to a unit dose form comprising about 10 to about 50 mg of a compound of Formula IIA and about 0 to about 0.15 mg of a compound of Formula II. In one embodiment, the invention relates to a unit dose form comprising about 20 to about 100 mg of a compound of Formula IIA and about 0 to about 0.25 mg of a compound of Formula II.

DEFINITIONS

Listed below are definitions of various terms used to describe this invention. These definitions apply to the terms as they are used throughout this specification and claims, unless otherwise limited in specific instances, either individually or as part of a larger group.

The term "aliphatic group" or "aliphatic" refers to a non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

The term "acyl" refers to a carbonyl substituted with hydrogen, alkyl, partially saturated or fully saturated cycloalkyl, partially saturated or fully saturated heterocycle, aryl, or heteroaryl. For example, acyl includes groups such as ($C_1$-$C_6$) alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" is intended to include both branched and straight chain, substituted or unsubstituted saturated aliphatic hydrocarbon radicals/groups having the specified number of carbons. Preferred alkyl groups comprise about 1 to about 24 carbon atoms ("$C_1$-$C_{24}$") preferably about 7 to about 24 carbon atoms ("$C_7$-$C_{24}$"), preferably about 8 to about 24 carbon atoms ("$C_8$-$C_{24}$"), preferably about 9 to about 24 carbon atoms ("$C_9$-$C_{24}$"). Other preferred alkyl groups comprise at about 1 to about 8 carbon atoms ("$C_1$-$C_8$") such as about 1 to about 6 carbon atoms ("$C_1$-$C_6$"), or such as about 1 to about 3 carbon atoms ("$C_1$-$C_3$"). Examples of $C_1$-$C_6$ alkyl radicals include, but are not limited to, methyl, ethyl, propyl, isopropyl, n-butyl, tert-butyl, n-pentyl, neopentyl and n-hexyl radicals.

The term "alkenyl" refers to linear or branched radicals having at least one carbon-carbon double bond. Such radicals preferably contain from about two to about twenty-four carbon atoms ("$C_2$-$C_{24}$") preferably about 7 to about 24 carbon atoms ("$C_7$-$C_{24}$"), preferably about 8 to about 24 carbon atoms ("$C_8$-$C_{24}$"), and preferably about 9 to about 24 carbon atoms ("$C_9$-$C_{24}$"). Other preferred alkenyl radicals are "lower alkenyl" radicals having two to about ten carbon atoms ("$C_2$-$C_{10}$") such as ethenyl, allyl, propenyl, butenyl and 4-methylbutenyl. Preferred lower alkenyl radicals include 2 to about 6 carbon atoms ("$C_2$-$C_6$"). The terms "alkenyl", and "lower alkenyl", embrace radicals having "cis" and "trans" orientations, or alternatively, "E" and "Z" orientations.

The term "alkynyl" refers to linear or branched radicals having at least one carbon-carbon triple bond. Such radicals preferably contain from about two to about twenty-four carbon atoms ("$C_2$-$C_{24}$") preferably about 7 to about 24 carbon atoms ("$C_7$-$C_{24}$"), preferably about 8 to about 24 carbon atoms ("$C_8$-$C_{24}$"), and preferably about 9 to about 24 carbon atoms ("$C_9$-$C_{24}$"). Other preferred alkynyl radicals are "lower alkynyl" radicals having two to about ten carbon atoms such as propargyl, 1-propynyl, 2-propynyl, 1-butyne, 2-butynyl and 1-pentynyl. Preferred lower alkynyl radicals include 2 to about 6 carbon atoms ("$C_2$-$C_6$").

The term "cycloalkyl" refers to saturated carbocyclic radicals having three to about twelve carbon atoms ("$C_3$-$C_{12}$"). The term "cycloalkyl" embraces saturated carbocyclic radicals having three to about twelve carbon atoms. Examples of such radicals include cyclopropyl, cyclobutyl, cyclopentyl and cyclohexyl.

The term "cycloalkenyl" refers to partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkylene," as used herein, refers to a divalent group derived from a straight chain or branched saturated hydrocarbon chain having the specified number of carbons atoms. Examples of alkylene groups include, but are not limited to, ethylene, propylene, butylene, 3-methyl-pentylene, and 5-ethyl-hexylene.

The term "alkenylene," as used herein, denotes a divalent group derived from a straight chain or branched hydrocarbon moiety containing the specified number of carbon atoms having at least one carbon-carbon double bond. Alkenylene groups include, but are not limited to, for example, ethenylene, 2-propenylene, 2-butenylene, 1-methyl-2-buten-1-ylene, and the like.

The term "alkynylene," as used herein, denotes a divalent group derived from a straight chain or branched hydrocarbon moiety containing the specified number of carbon atoms having at least one carbon-carbon triple bond. Representative alkynylene groups include, but are not limited to, for example, propynylene, 1-butynylene, 2-methyl-3-hexynylene, and the like.

The term "alkoxy" refers to linear or branched oxy-containing radicals each having alkyl portions of one to about twenty-four carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" refers to alkyl radicals having one or more alkoxy radicals attached to the alkyl radical, that is, to form monoalkoxyalkyl and dialkoxyalkyl radicals.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

The terms "heterocyclyl", "heterocycle", "heterocyclic" or "heterocyclo" refer to saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" refers to unsaturated aromatic heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" refers to heterocyclo-substituted alkyl radicals. More preferred heterocycloalkyl radicals are "lower heterocycloalkyl" radicals having one to six carbon atoms in the heterocyclo radical.

The term "alkylthio" refers to radicals containing a linear or branched alkyl radical, of one to about ten carbon atoms attached to a divalent sulfur atom. Preferred alkylthio radicals have alkyl radicals of one to about twenty-four carbon atoms or, preferably, one to about twelve carbon atoms. More preferred alkylthio radicals have alkyl radicals which are "lower alkylthio" radicals having one to about ten carbon atoms. Most preferred are alkylthio radicals having lower alkyl radicals of one to about eight carbon atoms. Examples of such lower alkylthio radicals include methylthio, ethylthio, propylthio, butylthio and hexylthio.

The terms "aralkyl" or "arylalkyl" refer to aryl-substituted alkyl radicals such as benzyl, diphenylmethyl, triphenylmethyl, phenylethyl, and diphenylethyl.

The term "aryloxy" refers to aryl radicals attached through an oxygen atom to other radicals.

The terms "aralkoxy" or "arylalkoxy" refer to aralkyl radicals attached through an oxygen atom to other radicals.

The term "aminoalkyl" refers to alkyl radicals substituted with amino radicals. Preferred aminoalkyl radicals have alkyl radicals having about one to about twenty-four carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene". Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

The phrase "minimum stirrable volume" refers to a solution or sludge that can be stirred with a stirrer or a paddle or a stirring device that has some amount of solvent still left in the mixture along with a solute. Generally, such solution/sludge results from evaporating/reducing a solvent in a solution where the reduction of solvent has not completely removed the solvent, but left the mixture in a reduced state where the mixture can be still stirred using a conventional method.

Substituents indicated as attached through variable points of attachments can be attached to any available position on the ring structure.

Virtually all of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, as well as their racemic and optically pure forms. When the compounds described herein contain olefinic double bonds or other centers of geometric asymmetry, and unless specified otherwise, it is intended that the compounds include both E and Z geometric isomers. Likewise, all tautomeric forms are also intended to be included.

The configuration of the newly created chiral center at nitrogen is arbitrarily depicted. In some cases the depiction may suggest R and in some it may suggest S. These depictions should not be taken as indicating that the absolute stereochemistry has been determined. It will be appreciated that the alkylation of the nitrogen to form a chiral molecule (as most are) is likely to prefer one isomer. If it were desired, this isomer and/or any racemic or diastereoisomeric mixture can be recovered or produced by techniques well known to those of skill in the art. Further, several chiral carbons are possible as well. Unless expressly otherwise stated in the claim, the claims are intended to encompass both or all isomers and mixtures, irrespective of whether the claim employs a formula which depicts the chirality of a center.

Example 1

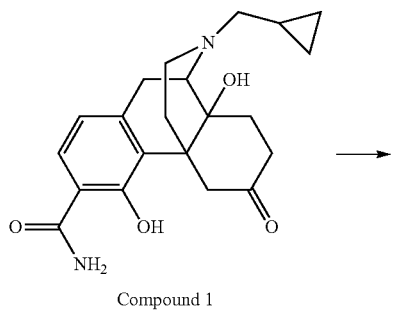

Compound 1

-continued

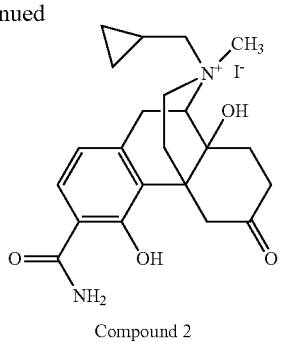

Compound 2

A pressure reactor under inert atmosphere was charged with acetonitrile (200 mL), Sodium carbonate (1 g) and Compound-1 (10 g). Methyl Iodide (17 mL) was added to the reactor. The mixture heated to between 70° C. and 75° C. with constant stirring for 14 to 30 hours. Upon reaction completion as determined by HPLC, the reactor contents were cooled to ambient temperature and filtered providing Compound 2 as pale yellow solid. The solids were washed with acetonitrile (10 mL, 1 vol.) and dried in vacuo at 30-35° C. to give Compound-2 (12 g, 87% yield).

H$^1$NMR (400 MHz, D$_6$-DMSO):

14.51 (1H), 8.58 (1H), 8.01 (1H), 7.80 (1H, d, 8.4 Hz), 6.73 (1H, d 8.4 Hz), 6.69 (1H), 4.09 (br-m, 1H), 3.90 (1H, d 13.5 Hz), 3.80 (1H, dd, 13.7, 4.7 Hz), 3.65 (s, 3H), 3.44 (2H, d, 1.9 Hz), 3.26 (1H, br-d, 12.9 Hz), 2.97 (1H, dd, 13.9, 9.2 Hz), 2.79 (1H, d, 13.9 Hz), 2.70 (m, 1H), 2.61 (1H, br-dd, 13.5, 10.9 Hz), 2.45 (1H, br-dd, 15.9, 12.7 Hz), 2.18 (1H, dd, 12.6, 6.6 Hz), 1.95 (1H, m), 1.87 (1H, m), 1.78 (1H, m), 1.19 (1H, m), 0.75 (1H, m), 0.70 (1H, m), 0.58 (1H, m), 0.38 (1H, m).

Example 2

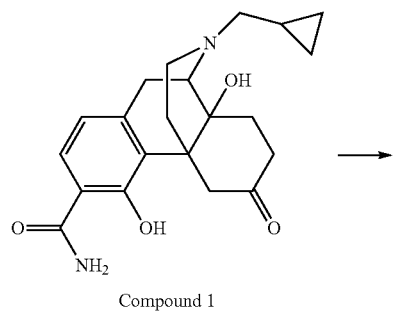

Compound 1

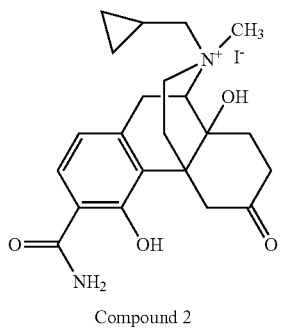

Compound 2

A pressure reactor under inert atmosphere was charged with acetonitrile (5 mL), Sodium bicarbonate (0.03 g) and Compound-1 (1 g). Methyl Iodide (0.6 mL) was added to the reactor. The mixture heated to between 70° C. and 75° C. with constant stirring for 14 to 30 hours. Upon reaction completion as determined by HPLC, the reactor contents were cooled to ambient temperature and filtered providing Compound 2 as pale yellow solid. The solids were washed with acetonitrile (5 mL, 1 vol.) and dried in vacuo at 30-35° C. to give Compound-2 (0.49 g, 89% yield).

H$^1$NMR (400 MHz, D$_6$-DMSO):

14.51 (1H), 8.58 (1H), 8.01 (1H), 7.80 (1H, d, 8.4 Hz), 6.73 (1H, d 8.4 Hz), 6.69 (1H), 4.09 (br-m, 1H), 3.90 (1H, d 13.5 Hz), 3.80 (1H, dd, 13.7, 4.7 Hz), 3.65 (s, 3H), 3.44 (2H, d, 1.9 Hz), 3.26 (1H, br-d, 12.9 Hz), 2.97 (1H, dd, 13.9, 9.2 Hz), 2.79 (1H, d, 13.9 Hz), 2.70 (m, 1H), 2.61 (1H, br-dd, 13.5, 10.9 Hz), 2.45 (1H, br-dd, 15.9, 12.7 Hz), 2.18 (1H, dd, 12.6, 6.6 Hz), 1.95 (1H, m), 1.87 (1H, m), 1.78 (1H, m), 1.19 (1H, m), 0.75 (1H, m), 0.70 (1H, m), 0.58 (1H, m), 0.38 (1H, m).

Example 3

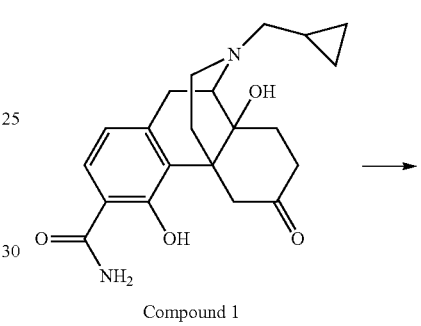

Compound 1

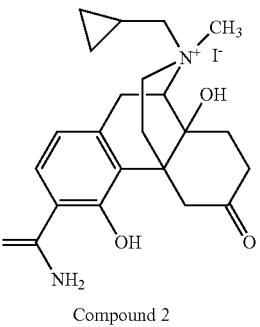

Compound 2

A pressure reactor under inert atmosphere was charged with acetonitrile (5 mL), triethylamine (0.05 mL) and Compound-1 (1 g). Methyl Iodide (0.6 mL) was added to the reactor. The mixture heated to between 70° C. and 75° C. with constant stirring for 14 to 30 hours. Upon reaction completion as determined by HPLC, the reactor contents were cooled to ambient temperature and filtered providing Compound 2 as pale yellow solid. The solids were washed with acetonitrile (5 mL, 1 vol.) and dried in vacuo at 30-35° C. to give Compound-2 (0.47 g, 85% yield).

H$^1$NMR (400 MHz, D$_6$-DMSO):

14.51 (1H), 8.58 (1H), 8.01 (1H), 7.80 (1H, d, 8.4 Hz), 6.73 (1H, d 8.4 Hz), 6.69 (1H), 4.09 (br-m, 1H), 3.90 (1H, d 13.5 Hz), 3.80 (1H, dd, 13.7, 4.7 Hz), 3.65 (s, 3H), 3.44 (2H, d, 1.9 Hz), 3.26 (1H, br-d, 12.9 Hz), 2.97 (1H, dd, 13.9, 9.2 Hz), 2.79 (1H, d, 13.9 Hz), 2.70 (m, 1H), 2.61 (1H, br-dd, 13.5, 10.9 Hz), 2.45 (1H, br-dd, 15.9, 12.7 Hz), 2.18 (1H, dd, 12.6, 6.6 Hz), 1.95 (1H, m), 1.87 (1H, m), 1.78 (1H, m), 1.19 (1H, m), 0.75 (1H, m), 0.70 (1H, m), 0.58 (1H, m), 0.38 (1H, m).

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A process for the synthesis of a compound of Formula IIA by quaternization of a compound of Formula II:

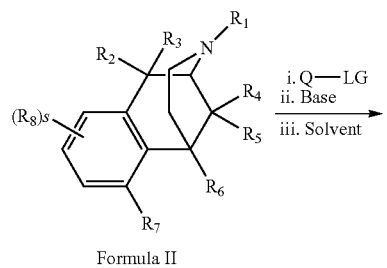

Formula II

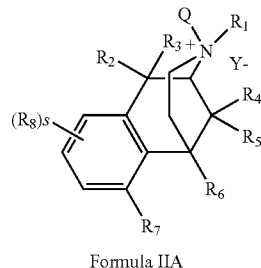

Formula IIA wherein, s is 0, 1, 2 or 3;

Y— is a pharmaceutically acceptable counterion;

each $R_1$, $R_2$, $R_3$, $R_4$, $R_7$ and $R_8$ is independently selected from hydrogen, halogen, —$OR_{20}$, —$SR_{20}$, —$NR_{20}R_{21}$, —$C(O)R_{20}$, —$C(O)OR_{20}$, —$C(O)NR_{20}R_{21}$, —$N(R_{20})C(O)R_{21}$, —$CF_3$, —CN, —$NO_2$, —$N_3$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl, substituted aryl, heterocyclyl or substituted heterocyclyl;

$R_5$, and $R_6$ together with the atoms they are attached form one additional optionally substituted ring;

alternatively $R_2$ and $R_3$ together with the carbon they are attached to form a C=X group;

wherein each $R_{20}$ and $R_{21}$ is independently selected from hydrogen, halogen, —OH, —SH, —$NH_2$, —$CF_3$, —CN, —$NO_2$, —$N_3$, —C(O)OH, —C(O)$NH_2$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl;

X is S, O or C($R_{20}$)($R_{21}$); and,

Q is aliphatic, substituted aliphatic, aryl, substituted aryl, heterocyclyl or substituted heterocyclyl;

wherein the quaternization process comprises the step of reacting a compound of Formula II with Q-LG in the presence of a base and a solvent, wherein LG is a leaving group;

wherein said compound of Formula IIA is insoluble in said solvent.

2. A process for the synthesis of a compound of Formula IIIA by quaternization of a compound of Formula III:

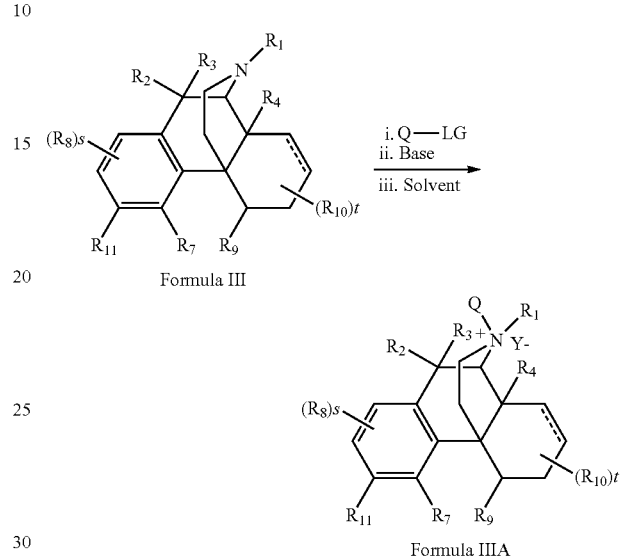

Formula III

Formula IIIA wherein;

s is 0, 1, 2 or 3;

Y— is a pharmaceutically acceptable counterion;

each $R_1$, $R_2$, $R_3$, $R_4$, $R_7$ and $R_8$ is independently selected from hydrogen, halogen, —$OR_{20}$, —$SR_{20}$, —$NR_{20}R_{21}$, —$C(O)R_{20}$, —$C(O)OR_{20}$, —$C(O)NR_{20}R_{21}$, —$N(R_{20})C(O)R_{21}$, —$CF_3$, —CN, —$NO_2$, —$N_3$ acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl, substituted aryl, heterocyclyl or substituted heterocyclyl;

Alternatively $R_2$ and $R_3$ together with the carbon they are attached to form a C=X group;

Wherein each $R_{20}$ and $R_{21}$ is independently selected from hydrogen, halogen, —OH, —SH, —$NH_2$, —$CF_3$, —CN, —$NO_2$, —$N_3$—C(O)OH, —C(O)$NH_2$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl;

t is 0, 1, 2, 3, 4, 5, 6, or 7;

each $R_9$, $R_{10}$ and $R_{11}$ is independently selected from hydrogen, halogen, —$OR_{20}$, —$SR_{20}$, —$NR_{20}R_{21}$, —$C(O)R_{20}$, —$C(O)OR_{20}$, —$C(O)NR_{20}R_{21}$, —$N(R_{20})C(O)R_{21}$, —$CF_3$, —CN, —$NO_2$, —$N_3$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl, substituted aryl, heterocyclyl or substituted heterocyclyl;

alternatively two $R_{10}$ groups together with the carbon they are attached to form a C=X group; wherein the quaternization process comprises the step of reacting a compound of Formula III with Q-LG in the presence of a base and a solvent, wherein LG is a leaving group; wherein said compound of Formula IIIA is insoluble in said solvent.
3. The process according to claim 1, wherein said quaternization process is selected from methylation of a tertiary amine from Processes 1 and 11-18:
Process 1:
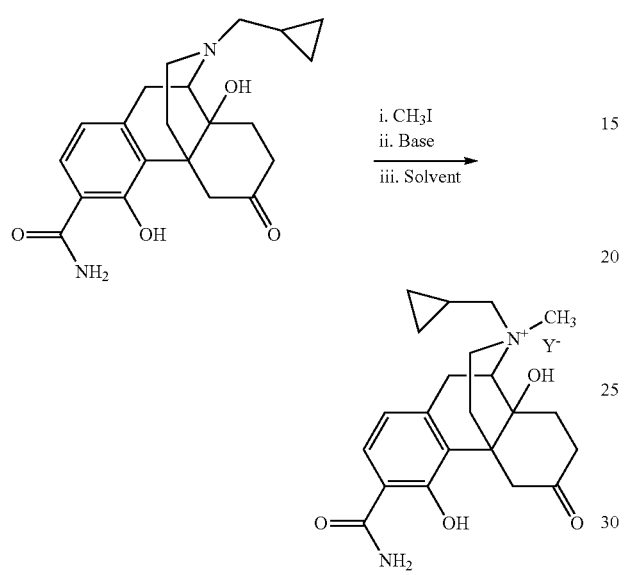
Process 11:
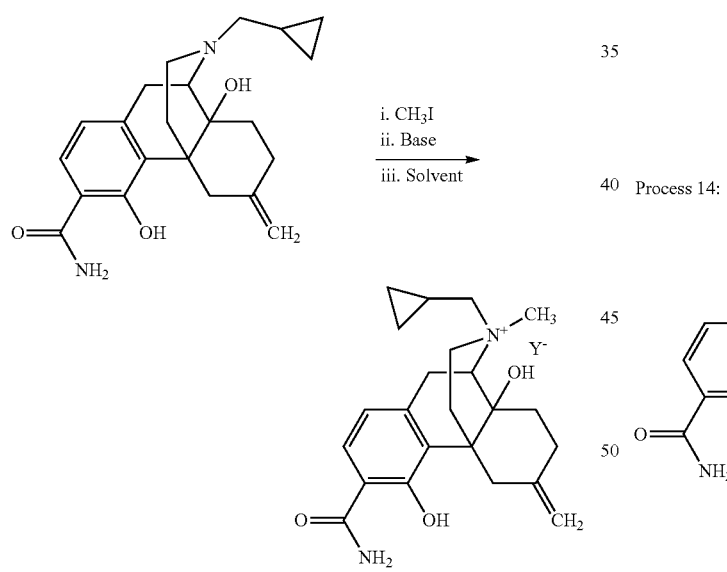
Process 12:
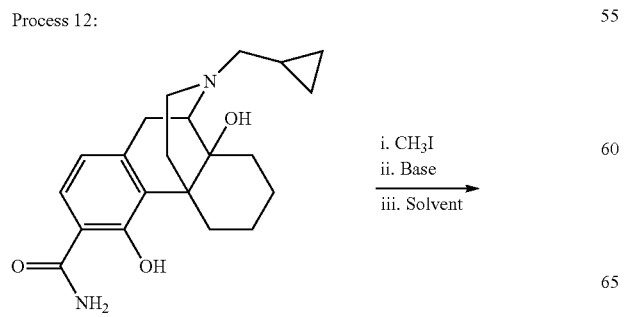
-continued
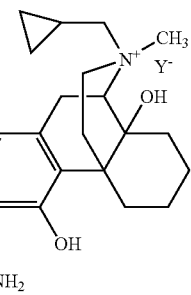
Process 13:
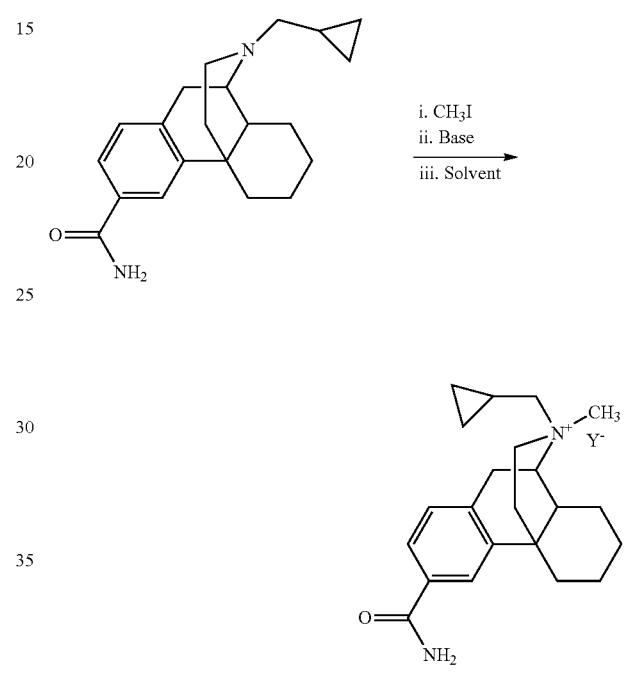
Process 14:
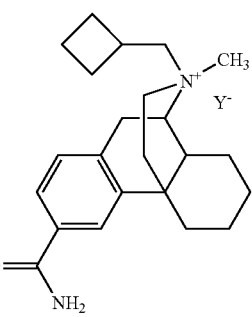

Process 15:

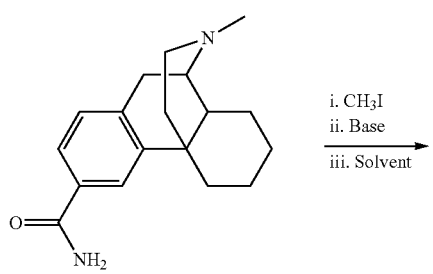

i. CH₃I
ii. Base
iii. Solvent
→

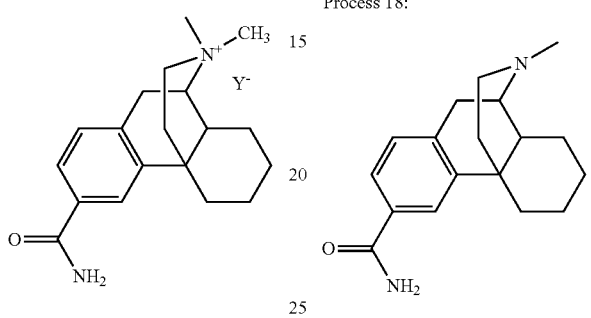

Process 16:

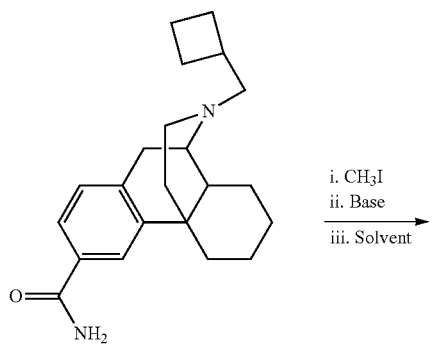

i. CH₃I
ii. Base
iii. Solvent
→

Process 17:

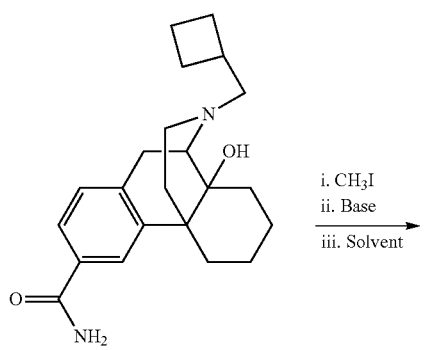

i. CH₃I
ii. Base
iii. Solvent
→

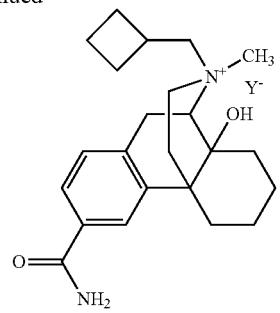

Process 18:

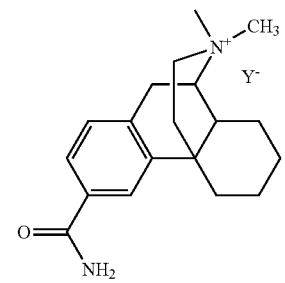

i. CH₃I
ii. Base
iii. Solvent
→

4. The process according to claim 1, wherein said base is selected from: triethyl amine, dimethyl amine, tert-butyl amine, aqueous ammonia, sodium hydroxide, calcium hydroxide, magnesium hydroxide, potassium hydroxide, lithium hydroxide, sodium carbonate, potassium carbonate, lithium carbonate, sodium bicarbonate, potassium bicarbonate, sodium tert-butoxide, sodium isopropoxide and potassium tert-butoxide.

5. The process according to claim 1, wherein Q-LG is an alkyl halide.

6. The process according to claim 1, wherein Q-LG is $CH_3$-LG, and LG is selected from bromide, chloride, iodide, alkyl sulfonate or aryl sulfonate, preferably mesylate or tosylate.

7. The process according to claim 1, wherein Q-LG is $CH_3CH_2$-LG, and LG is selected from bromide, chloride, iodide, alkyl sulfonate or aryl sulfonate, preferably mesylate or tosylate.

8. The process according to claim 1, wherein Y— is a halogen, substituted or unsubstituted alkylsulfonyl, substituted or unsubstituted arylsulfonyl, aliphatic, substituted aliphatic, aryl, substituted aryl, heterocyclyl or substituted heterocyclyl.

9. The process according to claim 1, wherein said solvent is a polar aprotic solvent or a non-polar solvent.

10. The process according to claim 9 wherein said polar aprotic solvent is selected from dichloromethane, tetrahydrofuran, ethyl acetate, acetone, N,N-dimethylformamide, acetonitrile, sulfolane, dimethylacetamide, N-methylpyrrolidine-2-one, isopropyl acetate, dimethylsulfoxide, nitromethane and mixtures thereof.

11. The process according to claim 1, wherein said solvent is acetonitrile.

12. The process according to claim 2, wherein said solvent is acetonitrile.

13. The process according to claim 3, wherein said solvent is acetonitrile.

\* \* \* \* \*